United States Patent
Van Note et al.

(10) Patent No.: US 7,168,283 B2
(45) Date of Patent: Jan. 30, 2007

(54) COBALT CHROME FORGING OF FEMORAL KNEE IMPLANTS AND OTHER COMPONENTS

(75) Inventors: Edward P. Van Note, Potterville, MI (US); Reaghn Azelton, East Lansing, MI (US)

(73) Assignee: AST Acquisitions, LLC, Holt, MI (US)

( * ) Notice: Subject to any disclaimer, the term of this patent is extended or adjusted under 35 U.S.C. 154(b) by 59 days.

(21) Appl. No.: 11/055,553

(22) Filed: Feb. 9, 2005

(65) Prior Publication Data

US 2006/0174678 A1    Aug. 10, 2006

Related U.S. Application Data

(60) Provisional application No. 60/542,982, filed on Feb. 9, 2004.

(51) Int. Cl.
*A61F 2/38* (2006.01)
(52) U.S. Cl. .............................. 72/364; 72/700; 72/356
(58) Field of Classification Search ................. 72/356, 72/360; 148/674; 623/20.14, 20.35
See application file for complete search history.

(56) References Cited

U.S. PATENT DOCUMENTS 4,887,179 A * 12/1989 Coe ........................... 360/135
5,560,096 A * 10/1996 Stephens ..................... 29/558
6,773,520 B1 * 8/2004 Fehring et al. ............. 148/425

OTHER PUBLICATIONS

"Replacing Parts on Nature's Machines" Puttre, Michael; Mechanical Engineering -CIME, v115, n5 p. 58(4); May 1993.*

* cited by examiner

*Primary Examiner*—Lowell A. Larson
*Assistant Examiner*—Debra Wolfe
(74) *Attorney, Agent, or Firm*—Thompson Hine LLP

(57) ABSTRACT

A method of creating a cobalt chronic femoral knee component includes the steps of: providing a forging press including first and second bust forging die parts spaced apart from each other and movable toward each other, the first and second bust forging die parts including respective femoral knee component shaped cavities; placing a cobalt chrome ingot heated to a temperature of between about 2050° F. and about 2300° F. between the first and second bust forging die parts in alignment with the femoral knee component shaped cavities; and bringing the first and second bust forging dies parts together in a bust blow against the cobalt chronic ingot under a pressure between about 1500 tons and 2000 tons creating a femoral knee bust forging. Additional steps may include cooling the femoral knee bust forging, heating the cooled femoral knee bust forging, providing a forging press with first and second block forging die parts, placing the heated femoral knee bust forging between the first and second block forging die parts, and bringing the first and second block forging die parts together in a block blow against the heated femoral knee bust component creating a femoral knee block forging.

9 Claims, 3 Drawing Sheets

COBALT CHROME FORGING OF FEMORAL KNEE IMPLANTS AND OTHER COMPONENTS

CROSS REFERENCE TO RELATED APPLICATION

This application claims priority to U.S. provisional application Ser. No. 60/542,982, filed Feb. 9, 2004, the entire contents of which are incorporated herein by reference.

TECHNICAL FIELD

The present application relates generally to manufacture of femoral knee implants and other components having complex shapes and, more particularly, to a cobalt chrome forging technique for producing such components.

BACKGROUND

Traditional techniques for manufacturing cobalt chrome components of complex shapes involve casting and/or metal injection molding methods. While a desire to forge such complex shapes using cobalt chrome materials has existed, the plastic deformation characteristics of cobalt chrome have proven problematic. Cast and metal injection formed cobalt chrome components tend to have less strength than a similarly sized and shaped forged cobalt chrome component.

Accordingly, it would be desirable to manufacture complex components, such as femoral knee implants, using a suitable cobalt chrome forging technique.

DETAILED DESCRIPTION

Figure 1:
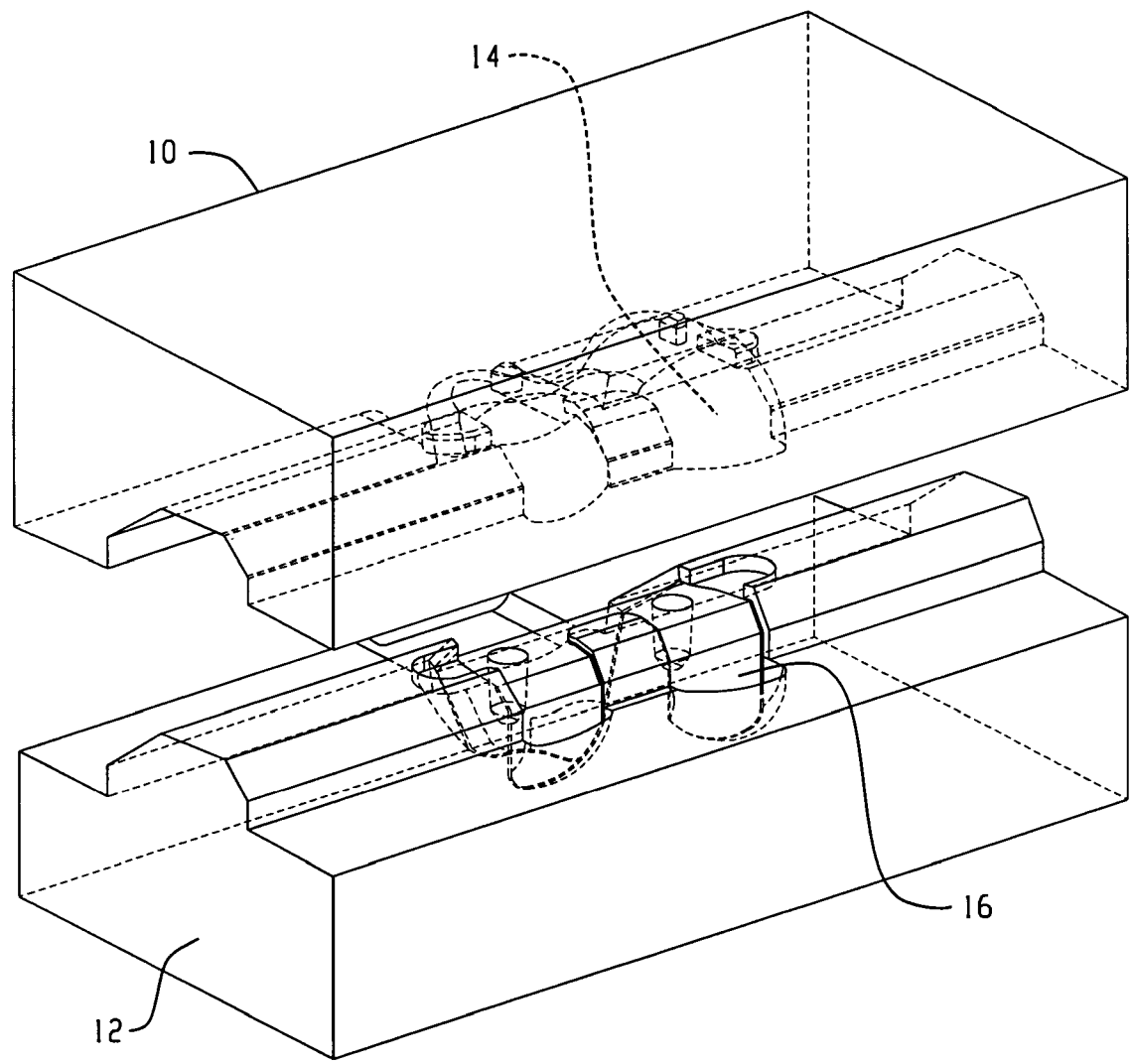
FIG. 1 illustrates die parts used to forge a femoral knee component.

Referring to FIG. 1, upper and lower die parts 10 and 12 are shown for use in forging a femoral knee component. Each die part includes a cavity 14, 16 therein configured in the general shape of the desired configuration of a portion of the femoral knee component. As illustrated, each cavity 14, 16 is of a fairly complex geometry. When the dies parts 10 and 12 are positioned adjacent each other, the cavities 14, 16 combine to create an overall cavity configured in the general shape of the entire femoral knee component.

In the forging process of the invention a first set of die parts may be used for a "bust" blow on a cobalt chrome ingot placed between the die parts. The cobalt chrome ingot may be heated to between about 2050° F. and 2300° F. using a suitable oven. In one implementation the cobalt chrome ingot may be heated to at least 2100° F. In another implementation the cobalt chrome ingot may be heated to at least 2150° F. In still another implementation the cobalt chrome ingot may be heated to at least 2200° F. In any of these implementations the cobalt chrom ingot may be heated no higher than 2300° F. in one example, 2275° F. in another example, 2250° F. in another example or no higher than 2225° F. in yet another example.

The bust forging die parts are incorporated into a forging press, such as a German Hassenclever 315 press, that brings the die parts together against a cobalt chrome ingot under a pressure of between about 1500 tons and 2000 tons causing the cobalt chrome ingot to flow within the cavity and creating a femoral knee bust component. In one implementation the pressure may at least about 1600 tons, in another implementation the pressure may be at least about 1700 tons, in another implementation the pressure may be at least about 1750 tons, in another implementation the pressure may be at least about 1800 tons, in another implementation the pressure may be at least about 1850 tons and in still another implementation the pressure may be at least about 1900 tons. The femoral knee bust component is then removed from the press and cooled (e.g., to ambient/room temperature), as by placement in water, and checked for defects, which are removed. The femoral knee bust component is then heated again to between about 2000° F. and 2300° F. to create a heated femoral knee bust component in preparation for a second, block forging blow. In one implementation the bust component may be heated to at least 2050° F., in another implementation the bust component may be heated to at least 2100° F., in another implementation the bust component may be heated to at least 2150° F. and in still another implementation the bust component may be heated to at least 2200° F. In any of these implementations the bust component may be heated no higher than 2300° F. in one example, 2275° F. in another example, 2250° F. in another example or no higher than 2225° F. in yet another example.

A second set of die parts may be used for the "block" blow against the heated femoral knee bust component. Typically, the cavity detail and dimension of the block forging die parts will be closer to desired finished component configuration and dimension than the cavity detail of the bust forging die parts. The block forging die parts are brought together against the heated femoral knee bust component under a pressure of between about 1500 tons and 2000 tons creating a femoral knee block component, which may be of a near net shape. In one implementation the pressure may at least about 1600 tons, in another implementation the pressure may be at least about 1700 tons, in another implementation the pressure may be at least about 1750 tons, in another implementation the pressure may be at least about 1800 tons, in another implementation the pressure may be at least about 1850 tons and in still another implementation the pressure may be at least about 1900 tons.

Figure 2:
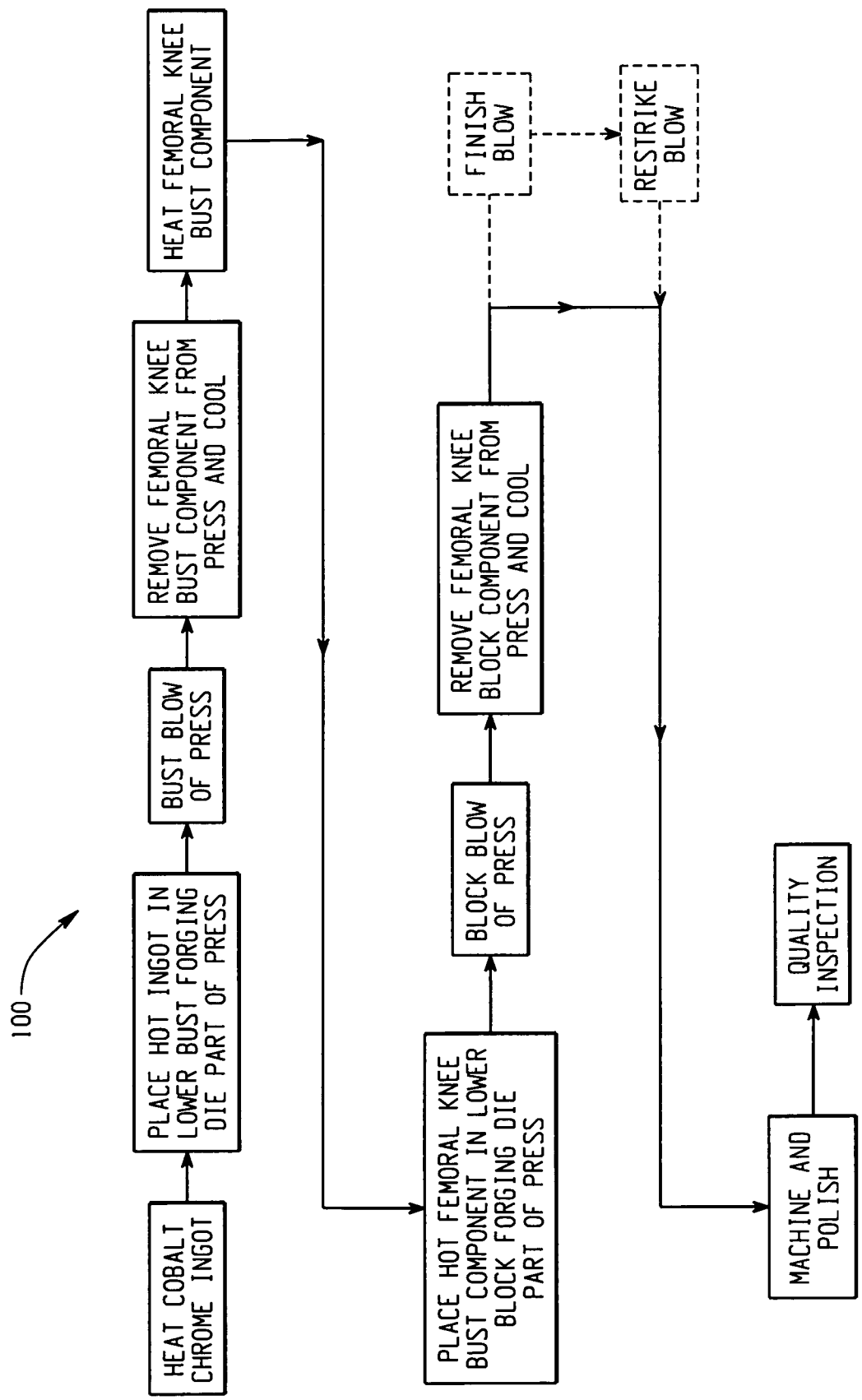
FIG. 2 illustrates a manufacturing process chart relating to the forging of a cobalt chrome femoral knee implant.
Figure 3:
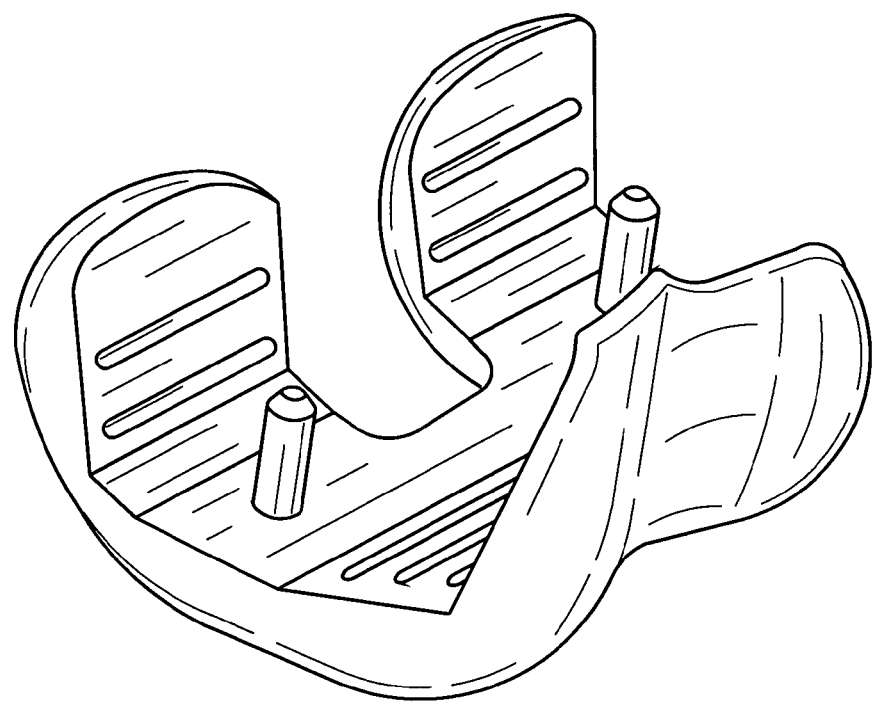
FIGS. 3 and 4 are perspective views illustrate an exemplary finished femoral knee implant.
Figure 4:
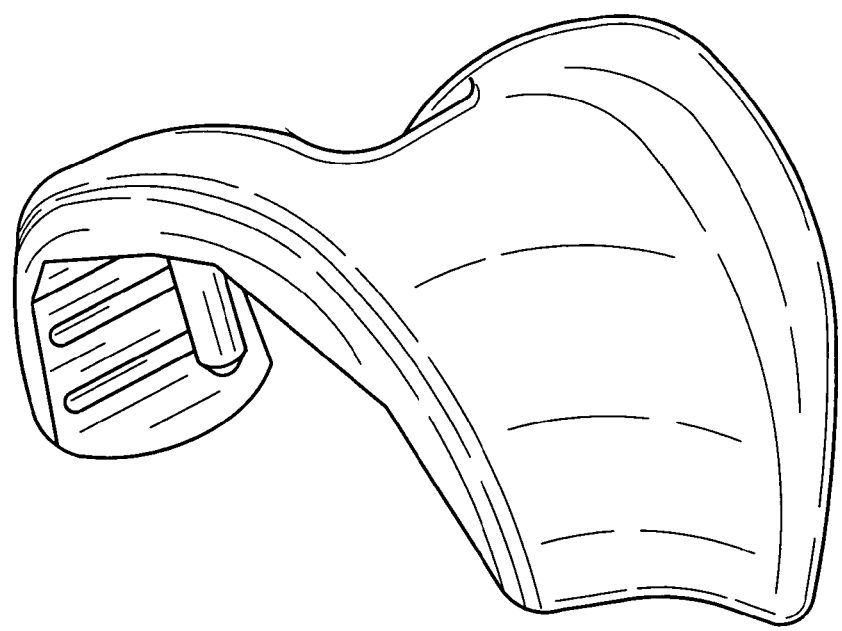

FIG. 2 shows an exemplary process diagram 100 for the above described manufacturing process.

In one embodiment, in the bust forging step the die part that defines the wear surface side of the component faces upward and in the block forging step the die part that defines the wear surface side of the component faces downward.

In one embodiment two different presses are used for the bust blow and the block blow, but it is recognized that the same press could be used. For example, in the case where a plurality of femoral knee bust components are produced using the press with a set of bust die parts, the femoral knee bust components are cooled, the press is then reconfigured with a set of block die parts and then the plurality of femoral knee bust components are heated and run through the block forging step.

In the illustrated embodiment the respective cavities of the upper and lower die parts are of a similar volume (both for the block forging step and for the bust forging step). Desirable forging may be achieved when at least forty percent (40%) of a volume of the femoral knee bust shape (which is defined by the adjacent cavities of bust forging die parts) is defined by the cavity of one bust forging die part and at least forty percent (40%) of the volume of the femoral knee bust shape is defined by the cavity of the other bust forging die part. In one implementation the volume split may be at least forty-five percent (45%) for the cavity defined by each bust forging die part. Likewise, desirable forging may be achieved when at least forty percent (40%) of a volume of the femoral knee block shape (which is defined by the adjacent cavities of block forging die parts) is defined by the cavity of the one block forging die part and at least forty percent (40%) of the volume of the femoral knee block shape is defined by the cavity of the other block forging die part. In one implementation the volume split may be at least forty-five percent (45%) for the cavity defined by each block forging die part.

Final processing of the femoral knee block component to achieve a finished femoral knee component may involve suitable machining and polishing. It is also possible that additional forging steps, including a finish forging blow and a restrike forging blow may be used, both steps being shown as optional steps in dashed line form in FIG. 2.

Applicants believe that by heating the cobalt chrome material to the temperatures noted above, and forging at the pressures noted above and utilizing dies with relatively evenly distributed cavity volumes as described above, the problems regarding plastic deformation characteristics of cobalt chrome can be suitably overcome. The resulting forged femoral knee component tends to have improved strength characteristics over a similar sized and shaped cobalt chrome component that is cast or metal injected. In particular, reference is made to the tables below showing test results for a component manufacture using a German Hassenclever 315 press and a Lucifer furnace.

TABLE 1

Cobalt Chrome Femoral Wrap Test Details - Anterior Angle

| Bust | 2250° F. |
|---|---|
| Finish | 2100° F. |
| Micro Grain size | Free & clear of carbides |
| Rc | Average 39.06 |
| Tensile psi | 200,800 |
| Yield psi | 128,900 |
| Elongation | 35.40% |
| Reduction | 29.40% |

Test reduction data for the anterior area of the component referenced in Table 1, is as follows, total area after hit one=0.635", total area after hit two=0.522", resulting in a total reduction of 0.113".

TABLE 2

Cobalt Chrome Femoral Wrap Test Details - Post Surface

| Bust | 2250° F. |
|---|---|
| Finish | 2100° F. |
| Micro Grain size | Free & clear of carbides |
| Rc | Average 39.06 |
| Tensile psi | 208,100 |
| Yield psi | 147,100 |
| Elongation | 35.40% |
| Reduction | 30.40% |

Test reduction data for the post area of the component referenced in Table 2, is as follows, total area after hit one=0.525", total area after hit two=0.450", resulting in a total reduction of 0.075". Rockwell hardness breakdown is shown in Table 3 below.

TABLE 3

Rockwell Data Breakdown

| Location | A | B | C | D | Avg. |
|---|---|---|---|---|---|
| Condile | 42 | 38 | 35 | 37 | 38 |
| Anterior Flange | 42 | 41 | 40 | 41 | 41 |
| 33 Degree angle | 41 | 40 | 42 | 39 | 41 |

Metal chemistry for the component reflected in the above table is set forth below in Table 4.

TABLE 4

Cobalt Chrome Chemistry

| Element | Weight % | Method |
|---|---|---|
| Carbon | 0.06 | E1019-00 |
| Manganese | 0.77 | E1251-94 (99) |
| Phosphorous | 0.017 | E1251-94 (99) |
| Sulfur | <0.005 | E1019-00 |
| Silicon | 0.54 | E1097-97 |
| Nickel | 0.31 | E1251-94 (99) |
| Chromium | 0.31 | E1251-94 (99) |
| Molybdenum | 5.18 | E1251-94 (99) |
| Aluminum | 0.08 | E1251-94 (99) |
| Tungsten | <0.05 | E1251-94 (99) |
| Boron | <0.005 | E1251-94 (99) |
| Iron | 0.55 | E1251-94 (99) |
| Nitrogen | 0.162 | E1937-97 |
| Titanium | <0.05 | E1251-94 (99) |
| Cobalt | Balance | E1251-94 (99) |

The foregoing constituent breakdown is exemplary only, and it is recognized that variations are possible for cobalt chrome materials. Exemplary suitable high carbon and low carbon cobalt chrome materials are available from Firth Rixon Alloys or Derbyshire, England, or Carpenter Specialty Alloys of Downers Grove, Ill., and are available under material specification numbers Biodur CCM+, Biodur CCM, HCCM-Hi carbon cobalt chrome, F799-LCCM.

By increasing the strength of the component utilizing forging technology verses casting/mim it is expected that the cross-section thickness can be substantially reduced thereby requiring 'less' bone removal of the femur during surgery to implant the femoral knee component. This end result is desirable because it will allow for a greater possibility of any revision surgery that might be required by a given patient in the future. Moreover, applicants believe that the more tightly compacted grains of a forging may prove to have superior abrasive resistance on the wear surface, and could reduce deterioration and debris of the polyethylene component that is typically the mating material to the cobalt wear surface.

It is to be clearly understood that the above description is intended by way of illustration and example only and is not intended to be taken by way of limitation, and that changes and modifications are possible.

What is claimed is:

1. A method of creating a cobalt chrome femoral knee component, comprising the steps of:
providing a forging press including first and second bust forging die parts spaced apart from each other and movable toward each other, the first and second bust forging die parts including respective femoral knee component shaped cavities;

placing a cobalt chrome ingot heated to a temperature of between about 2050° F. and about 2300° F. between the first and second bust forging die parts in alignment with the femoral knee component shaped cavities;

bringing the first and second bust forging dies parts together in a bust blow against the cobalt chrome ingot under a pressure of between about 1500 tons and 2000 tons creating a femoral knee bust forging;

cooling the femoral knee bust forging creating a cooled femoral knee bust forging;

heating the cooled femoral knee bust forging to a temperature of between about 2000° F. and 2300° F. creating a heated femoral knee bust forging;

providing a forging press with first and second block forging die parts spaced apart from each other and movable toward each other, the first and second block forging die parts including respective femoral knee component shaped cavities;

placing the heated femoral knee bust forging between the first and second block forging die parts in proper alignment with the femoral knee component shaped cavities;

bring the first and second block forging die parts together in a block blow against the heated femoral knee bust component under a pressure of between about 1500 tons and about 2000 tons creating a femoral knee block forging.

2. The method of claim 1 wherein the cavity of the first bust forging die part defines a wear surface side and the first bust forging die part faces upward toward the second bust forging die part, and the cavity of the first block forging die part defines a wear surface side and the first block forging component faces downward toward the second block forging die part.

3. The method of claim 1 wherein:

the cavity of the first bust forging die part and the cavity of the second bust forging die part combine when placed together to define a femoral knee bust shape, at least forty percent (40%) of a volume of the femoral knee bust shape is defined by the cavity of the first bust forging die part and at least forty percent (40%) of the volume of the femoral knee bust shape is defined by the cavity of the second bust forging die part; and the cavity of the first block forging die part and me cavity of the second block forging die part combine when placed together to define a femoral knee block shape, at least forty percent (40%) of a volume of the femoral knee block shape is defined by the cavity of the first block forging die part and at least forty percent (40%) of the volume of the femoral knee block shape is defined by the cavity of the second block forging die part.

4. A method of creating a cobalt chrome femoral knee component, comprising the steps of:

providing a forging press including first and second bust forging die parts spaced apart from each other and movable toward each other, the first and second bust forging die parts spaced apart from each other and movable toward each other, the first and second bust forging die parts including respective femoral knee component shaped cavities;

placing a cobalt chrome ingot heated to a temperature of between about 2050° F. and about 2300° F. between the first and second bust forging die parts in alignment with the femoral knee component shaped cavities;

bringing the first and second bust forging dies parts together in a bust blow against the cobalt chrome ingot under a pressure of between about 1500 tons and 2000 tons creating a femoral knee bust forging;

wherein the cavity of the first bust forging die part and the cavity of the second bust forging (40%) of a volume of the femoral knee bust shape is defined by the cavity of the first bust forging die part and at least forty percent (40%) of the volume of the femoral knee bust shape is defined by the cavity of the second bust forging die part.

5. The method of claim 1 wherein the cobalt chrome ingot is a low carbon cobalt chrome material.

6. The method of claim 1 wherein the cobalt chrome ingot is a high carbon cobalt chrome material.

7. A method of creating a cobalt chrome femoral knee implant, comprising the steps or:

providing a forging press including first and second bust forging die spaced parts from each other and movable toward each other, the first and second bust forging die parts including respective femoral knee component shaped cavities;

placing a quantity of cobalt chrome material, heated to a temperature of between about 2200° F. and about 2300° F. between the first and second bust forging die parts into one of the femoral knee component shaped cavities;

bringing the first and second bust forging dies parts together in a bust blow against the cobalt chrome material under a pressure of between about 1500 tons and 2000 tons creating a femoral knee bust forging;

cooling the femoral knee bust forging creating a cooled femoral knee bust forging;

heating the cooled femoral knee bust forging to a temperature of between about 2050° F. and 2225° F. creating a heated femoral knee bust forging;

providing a forging press with first and second block forging die parts including respective femoral knee component shaped cavities;

placing the heated femoral knee bust forging into an aligned position in one of the femoral knee component shaped cavities of the first and second block forging die parts;

bringing the first and second block forging die parts together in a block blow against the heated femoral knee bust component under a pressure of between about 1500 tons and about 2000 tons creating a femoral knee block forging.

8. The method of claim 7 comprising the further steps of:
machining and polishing to produce final configuration and surface finish of the femoral knee implant.

9. The method of claim 8 comprising the further step of:
applying one or both of a finish blow and a restrike after the block blow and before machining and polishing to final configuration and surface finish.

* * * * *

UNITED STATES PATENT AND TRADEMARK OFFICE
CERTIFICATE OF CORRECTION

PATENT NO.         : 7,168,283 B2
APPLICATION NO.    : 11/055553
DATED              : January 30, 2007
INVENTOR(S)        : Edward P. Van Note et al.

It is certified that error appears in the above-identified patent and that said Letters Patent is hereby corrected as shown below:

Item (57) Abstract

Line 1 – Change "chronic" to -- chrome --;

Line 11 – Change "chronic" to -- chrome --;

Line 12 – After "pressure" insert -- of--.

Col. 5

Line 44 Change "me" to -- the --;

Lines 58 – 60 – Delete the wording "spaced apart from each other and movable toward each other, the first and second bust forging die parts".

Col. 6

Line 10 – After "forging" insert -- die part combine when placed together to define a femoral knee bust shape, at least forty percent -- ;

Line 21 – Change "or" to -- of --;

Line 23 – After "die" insert -- parts --;

Line 23 – After "spaced" change "parts" to -- apart --;

Line 42 – After "parts" insert -- spaced apart from each other and movable toward each other, the first and second block forging die parts --;

UNITED STATES PATENT AND TRADEMARK OFFICE
CERTIFICATE OF CORRECTION

PATENT NO. : 7,168,283 B2
APPLICATION NO. : 11/055553
DATED : January 30, 2007
INVENTOR(S) : Edward P. Van Note et al.

It is certified that error appears in the above-identified patent and that said Letters Patent is hereby corrected as shown below:

Col. 6 (Cont.)

Line 57 – After "restrike" insert -- blow --.

Signed and Sealed this

Tenth Day of April, 2007

JON W. DUDAS
*Director of the United States Patent and Trademark Office*